United States Patent
Hatori

[11] Patent Number: 5,299,560
[45] Date of Patent: Apr. 5, 1994

[54] ENDOSCOPE IN WHICH A BEND REMAINING IN THE INSERTION PORTION UPON REMOVAL FROM STORAGE IS REDUCED

[75] Inventor: Tsuruo Hatori, Tokyo, Japan
[73] Assignee: Olympus Optical Co., Ltd., Tokyo, Japan
[21] Appl. No.: 900,991
[22] Filed: Jun. 18, 1992
[51] Int. Cl.⁵ .................................................. A61B 1/00
[52] U.S. Cl. ........................................ 128/4; 128/6; 385/117
[58] Field of Search ................ 128/4, 6, 7, 8, 10, 128/11, 772; 385/115, 117

[56] References Cited

U.S. PATENT DOCUMENTS

| | | |
|---|---|---|
| 3,434,775 | 3/1969 | Gosselin .............................. 385/118 |
| 4,576,145 | 3/1986 | Tsuno et al. . |
| 4,732,139 | 3/1988 | Kawashima et al. . |
| 4,756,303 | 7/1988 | Kawashima et al. . |
| 4,776,668 | 10/1988 | Fujimoto .............................. 128/4 X |
| 4,790,295 | 12/1988 | Tashiro .................................... 128/6 |
| 4,813,400 | 3/1989 | Washizuka ...................... 385/117 X |
| 4,921,326 | 5/1990 | Wild et al. ........................... 128/6 X |
| 4,945,894 | 8/1990 | Kawashima ............................. 128/6 |

FOREIGN PATENT DOCUMENTS

| | | |
|---|---|---|
| 61-277915 | 12/1986 | Japan . |
| 63-249537 | 10/1988 | Japan . |
| 63-180003 | 11/1988 | Japan . |
| 2-25816 | 1/1990 | Japan . |
| 2-189156 | 7/1990 | Japan . |

*Primary Examiner*—Richard J. Apley
*Assistant Examiner*—Karen A. Jalbert
*Attorney, Agent, or Firm*—Frishauf, Holtz, Goodman & Woodward

[57] ABSTRACT

There is disclosed an endoscope comprising an image guide fiber and a light guide fiber extending along the axis of an insertion portion, and an outer tube made of a synthetic resin material for covering contained matters consisting of the image guide fiber and the light guide fiber, the outer tube having the flexibility thereof higher than that of the image guide fiber and light guide fiber, thereby preventing remaining-bend of the insertion portion.

10 Claims, 4 Drawing Sheets

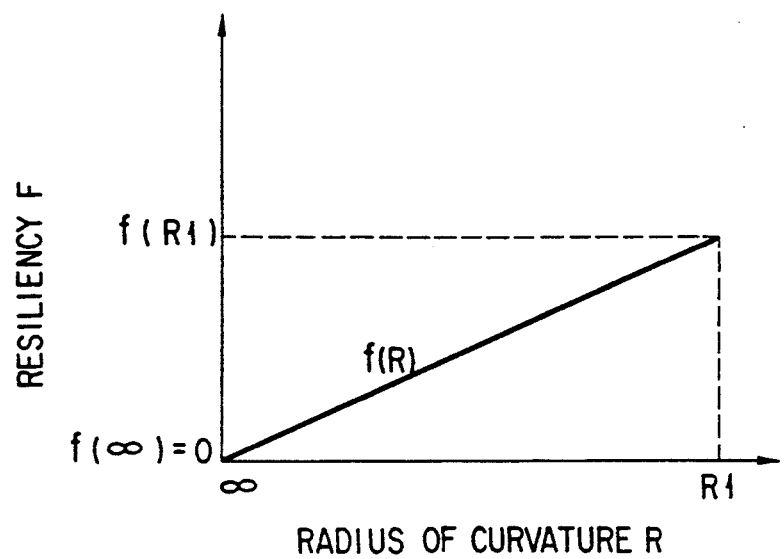
F I G. 4
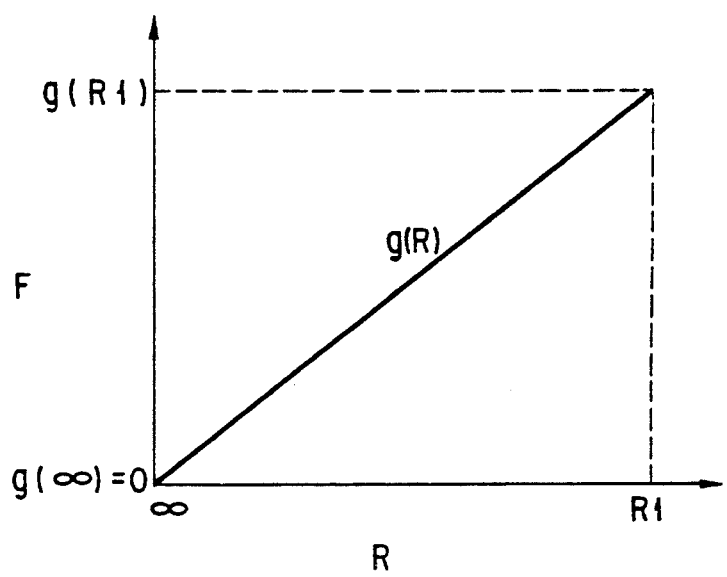
F I G. 5

ENDOSCOPE IN WHICH A BEND REMAINING IN THE INSERTION PORTION UPON REMOVAL FROM STORAGE IS REDUCED

BACKGROUND OF THE INVENTION

1. Field of the Invention

The present invention relates to an elastic endoscope having an insertion portion made of a flexible tube which is to be inserted into a body tube or a body cavity.

2. Description of the Related Art

Elastic endoscopes each having an insertion portion made of a flexible tube which is to be inserted into a body tube or a body cavity are disclosed, for example, in Published Unexamined Japanese Patent Application (PUJPA) No. 2-25816, Published Unexamined Japanese Utility Model Application (PUJUMA) No. 63-180003, and PUJPA No. 61-277915. In these prior-art endoscopes, an outer-sheath tube of the insertion portion is made of a viscoelastic material such as synthetic resin. Most of the characteristics of the insertion portion, such as flexibility and resiliency are determined by the characteristics of the synthetic resin itself of the outer-sheath tube.

The conditions of the outer-sheath tube of the insertion portion of the endoscope, e.g. softness of the outer-sheath tube, are determined in accordance with the state of a region-of-interest into which the end-oscope is inserted. A synthetic resin material having characteristics which meet the conditions is selected for each type of endoscope and is used as a material of its outer-sheath tube. For example, a relatively soft synthetic resin material is selected and used as material of the outer-sheath tube of the insertion portion of the endoscope to be inserted into a region-of-interest which requires softness of the outer-sheath tube. On the other hand, a relatively hard synthetic resin material is selected and used as material of the outer-sheath tube of the insertion portion of the endoscope to be inserted into a region-of-interest which requires suitable hardness of the outer-sheath tube, in order to achieve smooth insertion and easy operation of the endoscope.

In the meantime, the length of the insertion portion of the endoscope varies depending on the region-of-interest into which the endoscope is inserted. When the length of the insertion portion of the endoscope is relatively large, it is difficult to pack or store the endoscope in the state in which its insertion portion is extended substantially straight. In this case, the endoscope is packed or stored in the state in which the insertion portion is bent in a suitable shape or wound in a substantially annular shape.

However, in the conventional endoscope, the outer-sheath tube of the insertion portion is made of a viscoelastic resin material and has both elasticity and viscosity. Thus, the characteristics of the outer-sheath tube are influenced by temperatures and time, and such problems as creep or stress relaxation phenomenon tend to occur.

Consequently, when the endoscope is packed or stored in the state in which the insertion portion is bent in a suitable shape or wound in a substantially annular shape and the packed or stored endoscope is left for a long time, a stress relaxation phenomenon may occur. As a result, bending of the insertion portion of the endoscope remains even after the endoscope which has been in the packed or stored state for a long time is taken out of this state.

When bending of the insertion portion remains after it is taken out of the packed or stored state, insertion of the endoscope becomes difficult. Thus, smooth insertion and easy operation of the endoscope cannot be achieved.

SUMMARY OF THE INVENTION

The present invention has been made in consideration of the above circumstances, and its object is to provide an endoscope whereby the possibility that bending of an insertion portion bent at the time of packing and storage remains is reduced, and smoother insertion and easier operation of the insertion portion can be achieved.

In order to achieve the above object, there is provided an endoscope having an elastic insertion portion, comprising: an internal structural element extending along the axis of the insertion portion, the internal structural element being made of a non-viscoelastic material; and a sheath element covering the internal structural element, the sheath element being made of a viscoelastic material; the sheath having the flexibility thereof higher than that of the internal structural element, thereby preventing remaining-bend of the insertion portion.

According to the present invention, even if stress relaxation occurs in an outer-sheath tube of a viscoelastic material when an insertion portion of an endoscope is bent in a desired shape, a remaining bend of the outer-sheath tube is restored to the original state by a resiliency against a bend which acts on an internal structural element made of a non-viscoelastic material in which stress relaxation does not easily occur. Thereby, a remaining bend in the insertion portion is prevented, and smoother insertion and easier operation of the insertion portion can be achieved when the endoscope is used.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a graph showing the relationship between a radius R of curvature and resiliency F of an outer-sheath tube;

FIG. 5 is a graph showing the relationship between a radius R of curvature and resiliency F of an image guide fiber;

DETAILED DESCRIPTION OF THE PREFERRED EMBODIMENTS

FIGS. 1 to 6 show a first embodiment of the present invention.

Figure 1:
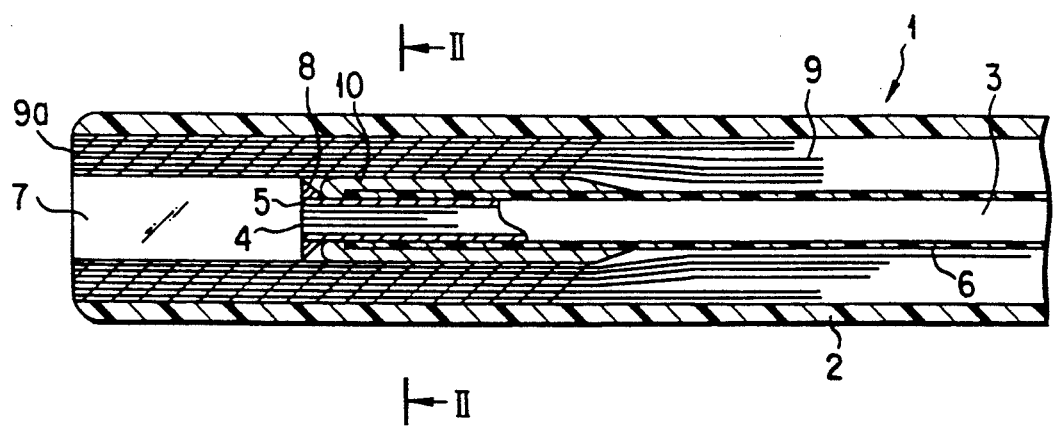
FIG. 1 is a vertical cross-sectional view showing the structure of an important portion of an insertion portion of an endoscope according to a first embodiment of the invention.

FIG. 1 shows the structure of an important portion of an insertion portion 1 of an endoscope. The insertion portion 1 includes an outer-sheath tube (outer-sheath element) 2 made of a viscoelastic material such as synthetic resin.

Figure 2:
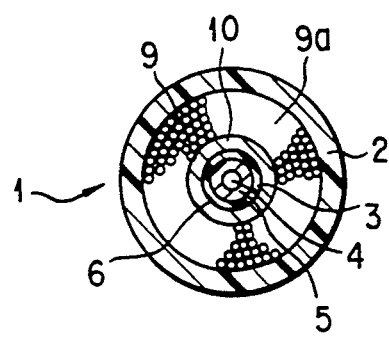
FIG. 2 is a cross-sectional view taken along line II—II in FIG. 1.

A conduit-type image guide fiber (internal structural element) 3 of a non-viscoelastic material such as quartz glass is arranged axially in a radially central area of the insertion portion 1. As is shown in FIG. 2, the image guide fiber 3 has a concentric three-layer structure. An effective picture element portion 4 in which a great number of optical fibers are sealed is situated at a central area of the three-layer structure. A jacket portion 5 surrounds the picture element portion 4. A coating portion 6 surrounds the jacket portion 5.

The picture element portion 4 and jacket portion 5 are quartz glass layers, and the coating portion 6 is a synthetic resin layer of, e.g. polyurethane. The coating portion 6 prevents growth of microcracks in the peripheral surface of the jacket portion 5. For example, when the image guide fiber 3 is bent, microcracks grow abruptly. The coating portion 6 prevents the image guide fiber 3 from being broken by the microcracks.

An objective lens 7 is situated at a radially central area of an end portion of the insertion portion 1. The objective lens 7 is formed of a heterogeneous medium lens element. An end face of the image guide fiber 3 is fixed to the objective lens 7 by an adhesive 8.

The image guide fiber 3 and objective lens 7 are surrounded by a light guide fiber (internal structural element) 9 made of a non-viscoelastic material. A cylindrical end fixing portion 9a (indicated by hatched lines in FIG. 1) fixed by an adhesive is formed at the end portion of the light guide fiber 9.

The objective lens 7 and the end portion of the image guide fiber 3 are inserted in a hollow cylindrical part of the end-fixing portion 9a. Mutual fixation among the end-fixing portion 9a of light guide fiber 9, the objective lens 7, and the end portion of image guide fiber 3 is effected by an adhesive 10.

The outer diameter of the objective lens 7 is greater than that of the coating portion 6 of the image guide fiber 3. The filling rate of matter contained in the outer-sheath tube 2 in a region where the image guide fiber 3 adjoins the light guide fiber 9 is lower than that of matter contained in the outer-sheath tube 2 in a region where the light guide fiber 9 adjoins the objective lens 7.

Further, the outer-sheath tube 2 is provided to surround the periphery of the light guide fiber 9. The inner peripheral surface of the end portion of the outer-sheath tube 2 is fixed to the outer peripheral surface of the end-fixing portion 9a of light guide fiber 9 by an adhesive. In this case, the flexibility (elasticity) of the outer-sheath tube 2 is set to be higher than that of internal structural elements such as image guide fiber 3 and light guide fiber 9.

The flexibility of the outer-sheath tube 2 can be set to be higher than that of internal structural elements such as image guide fiber 3 and light guide fiber 9, for example, by suitably controlling the relationship between the outer diameter of the jacket portion 5 of image guide fiber 3 and the wall thickness of the outer-sheath tube 2. Specifically, the outer diameter of the jacket portion 5 of image guide fiber 3 is determined relative to the wall thickness of the outer-sheath tube 2 such that the flexibility of the internal structural elements becomes lower than that of the outer-sheath tube 2. Alternatively, the outer-sheath tube 2 may be made of a material having a higher flexibility than the material of the internal structural elements.

Next, the flexibility of the outer-sheath tube 2 and the internal structural elements such as image guide fiber 3 will now be described.

Figure 3:
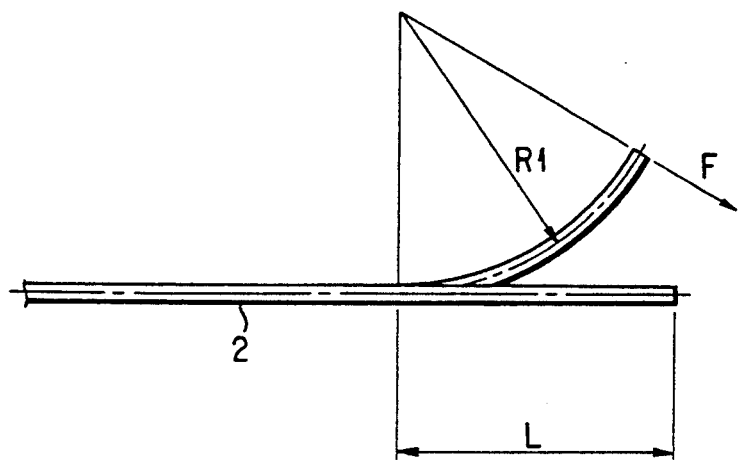
FIG. 3 is a schematic view for illustrating the resiliency of an outer-sheath tube.

In FIG. 3, an upward force is applied to an end portion of the outer-sheath tube 2, which has a predetermined length L from the end of the tube 2. Thus, the end portion of the tube 2 is bent. In this case, the radius R of curvature of the end portion of the tube 2 and the resiliency F of the tube 2 have the relationship:

$$F = f(R)$$

As is shown in FIG. 4, as the radius R of curvature of the end portion of the outer-sheath tube 2 is decreased from infinity ($\infty$) to R1 (in FIG. 3), the resiliency of the outer-sheath tube 2 increases from f ($\infty$) to f (R1). In this case, the initial state is $$f(\infty) = 0$$

FIG. 4 shows a linear model.

Similarly, an upward force (in FIG. 3) is applied to an end portion of the image guide fiber 3, which has a predetermined length L from the end of the fiber 3. Thus, the end portion of the fiber 3 is bent. In this case, the radius R of curvature of the end portion of the image guide fiber 3 and the resiliency F of the fiber 3 have the relationship:

$$F = g(R)$$

As is shown in FIG. 5, as the radius R of curvature of the end portion of the image guide fiber 3 is decreased from infinity ($\infty$) to R1, the resiliency of the image guide fiber 3 increases from g ($\infty$) to g (R1). In this case, the initial state is $$g(\infty) = 0$$

At this time, since the flexibility of the image guide fiber 3 is lower than that of the outer-sheath tube 2, the radius R of curvature meets the following condition in range from the infinity ($\infty$) to R1:

$$g(R) > f(R)$$

The operation of the first embodiment having the above structure will now be described.

The outer-sheath tube 2 is formed of a synthetic resin or a viscoelastic material. Thus, if the insertion portion 1 of the endoscope is bent from its substantially straight basic shape and left for a long time, stress relaxation occurs in the outer-sheath tube 2.

Figure 6:
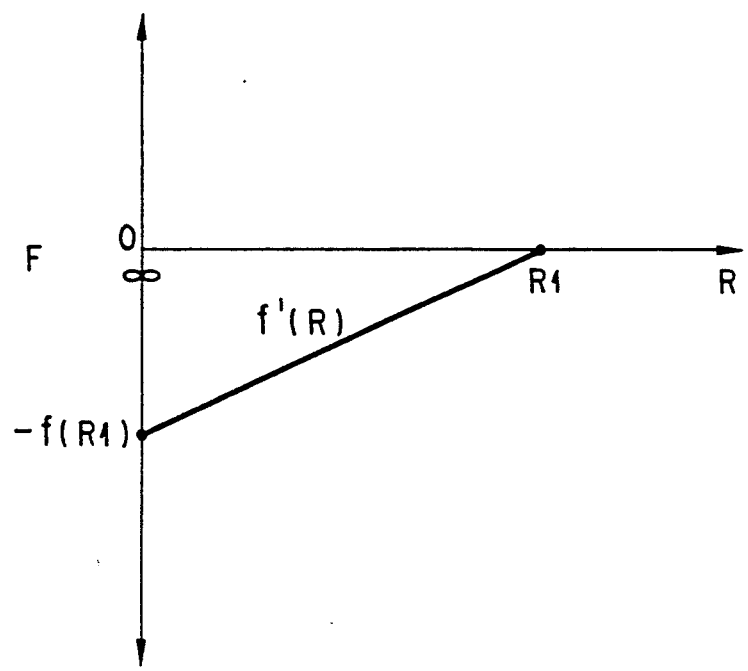
FIG. 6 is a graph showing the relationship between a radius R of curvature and resiliency F of an outersheath tube, for illustrating a stress relaxation phenomenon of the outer-sheath tube.

When the insertion portion 1 of the endoscope is left in the bent shape with the radius R1 of curvature, as shown in FIG. 3 and stress relaxation progresses, the resiliency F of the outer-sheath tube 2 becomes 0 in the state in which the radius R of curvature of the insertion portion 1 is R1. In this case, a resistance force in the outer-sheath tube 2 increases as the radius R of curvature of the insertion portion 1 is varied from R1 towards infinity ($\infty$), that is, as the insertion portion 1 is restored to the straight basic shape. The resistance force F' occurring in the outer-sheath tube 2 in which stress relaxation has progressed acts in a direction opposite to the direction of the resiliency F=f (R) of the tube 2. When the force F' is given by $$F = f(R)$$

its maximum value is f' (R)=f (R)−f (R1), as shown in FIG. 6.

The image guide fiber 3 in the insertion portion 1 of the endoscope is made of quartz glass or a non-viscoelastic material. Thus, even if the insertion portion 1 of the endoscope is bent from its substantially straight basic shape and left for a long time, stress relaxation does not easily occur and the relationship, F=g (R), is maintained.

Both the outer-sheath tube 2 of the viscoelastic material and the image guide fiber 3 of the non-viscoelastic material are commonly employed as structural elements of the insertion portion 1 of the endoscope. Thus, bending of the insertion portion 1, which is defined by the radius of curvature equaling f' (R) and g (R), remains. Supposing that the radius of curvature of the bending is r, the following is given:

$$g(r) = f(r) - f(R1)$$

In this case, the flexibility of the image guide fiber 3 is set to be lower than that of the outer-sheath tube 2, and the following relationship is established:

$$g(R) > f(R)$$

Thus, radius r of curvature of bending is close to the infinity ($\infty$), and bending of the insertion portion 1 of the endoscope does not easily remain. Accordingly, the possibility that bending of the insertion portion 1 bent at the time of packing and storage remains, as in the conventional endoscope, is reduced. In addition, smoother insertion and easier operation of the insertion portion 1 of the endoscope can be achieved.

Moreover, the outer diameter of the objective lens 7 is greater than that of the coating portion 6 of the image guide fiber 3, and the filling rate of matter contained in the outer-sheath tube 2 in a region where the image guide fiber 3 adjoins the light guide fiber 9 is lower than that of matter contained in the outersheath tube 2 in a region where the light guide fiber 9 adjoins the objective lens 7. Thus, when the insertion portion 1 of the endoscope is bent, the contact surfaces of the light guide fiber 9 and the image guide fiber 3 can be axially slid on each other within the outer-sheath tube 2. Accordingly, breakage of the image guide fiber 3 and light guide fiber 9 can be prevented.

Furthermore, since the filling rate of matter contained in the outer-sheath tube 2 in the region where the light guide fiber 9 adjoins the objective lens 7 is higher, inclination of the objective lens 7 can be prevented.

The above embodiment is based on the case where the stress relaxation of the outer-sheath tube 2 has progressed to a maximum level, wherein $$f(R) = f(R) - f(R1)$$

However, in fact, the stress relaxation does not progress to this level. Thus, actually remaining bending is defined by a radius of curvature greater than r.

In the above embodiment, the insertion portion 1 of the endoscope has a relatively simple structure constituted by the outer-sheath tube 2, image guide fiber 3 and light guide fiber 9. Needless to say, the structure of the insertion portion 1 is not limited to this, and various modifications may be made.

Figure 7:
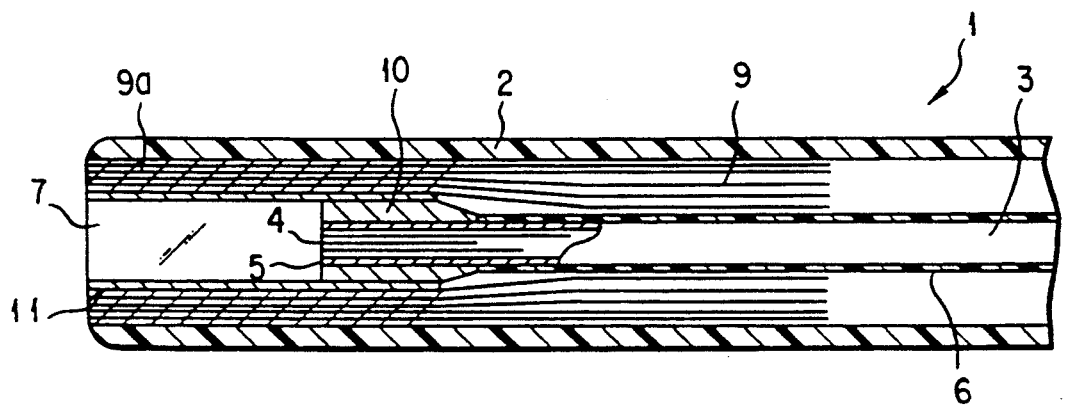
FIG. 7 is a vertical cross-sectional view showing an important portion according to a second embodiment of the invention.

FIG. 7 shows a second embodiment of the present invention. A cylindrical lens frame 11 is provided for holding the objective lens 7 constituted by a heterogeneous medium lens element. The objective lens 7 and the contact faces of the lens 7 and the image guide fiber 3 are contained within the lens frame 11. The outer diameter of the lens frame 11 is greater than that of the coating portion 6 of the image guide fiber 3.

In the second embodiment, like the first embodiment, the insertion portion 1 of the endoscope includes the outer-sheath tube 2 of the viscoelastic material and the image guide fiber 3 of the non-viscoelastic material. The flexibility of the image guide fiber 3 is set to be lower than that of the tube 2. Thus, like the first embodiment, a remaining bend does not easily occur in the insertion portion 1 of the endoscope. Accordingly, the possibility that bending of the insertion portion 1 bent at the time of packing and storage remains is reduced, and smoother insertion and easier operation of the insertion portion 1 of the endoscope can be achieved.

Further, since the contact faces of the lens 7 and the image guide fiber 3 are contained within the lens frame 11, an external force is not directly applied to the contact faces of the lens 7 and the image guide fiber 3. Thus, separation between the lens 7 and fiber 3 can be prevented.

Figure 8:
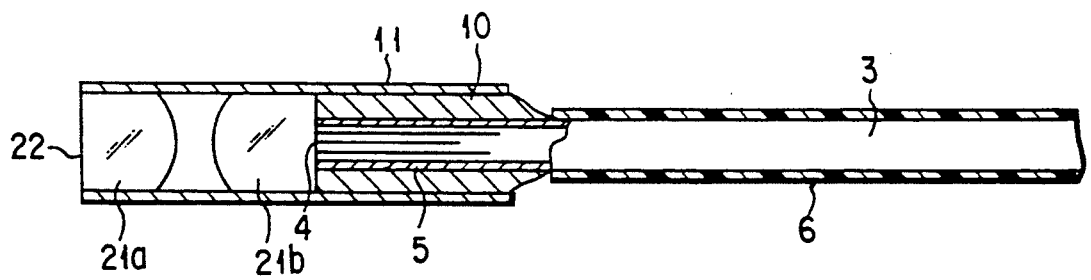
FIG. 8 is a vertical cross-sectional view showing an important portion according to a third embodiment of the invention.

FIG. 8 shows a third embodiment of the invention. An objective lens 22 constituted by a lens system in which two convex lenses 21a and 21b are combined is stored within the lens frame 11 according to the second embodiment shown in FIG. 7. Similarly, the contact faces between the rear convex lens 21b and the image guide fiber 3 are contained within the lens frame 11. With the third embodiment, the same advantages as in the second embodiment can be obtained.

Figure 9:
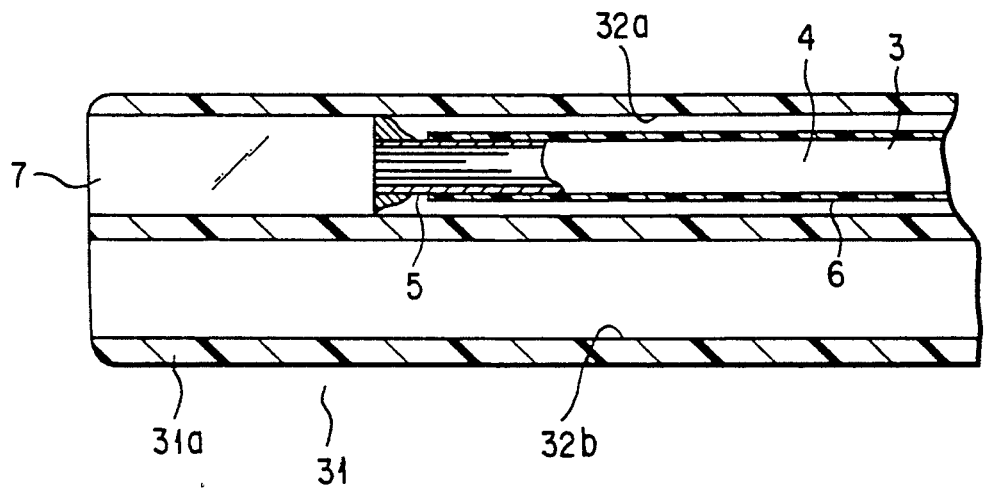
FIG. 9 is a vertical cross-sectional view showing an important portion according to a fourth embodiment of the invention.
Figure 10:
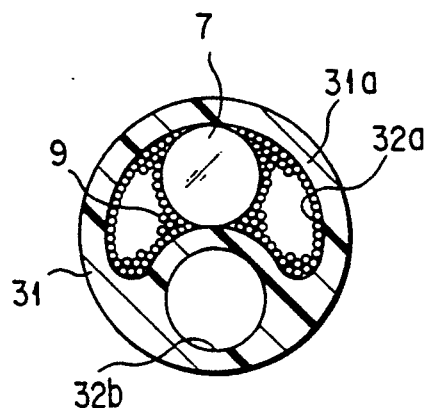
FIG. 10 is a plan view of an end face of the insertion portion according to the fourth embodiment of the invention.

FIGS. 9 and 10 show a fourth embodiment of the invention. In the fourth embodiment, the outer-sheath tube 2 of the first embodiment is replaced by a multi-lumen tube 31. The multi-lumen tube 31 has a plurality of holes (two holes 32a and 32b in this embodiment) extending axially within a flexible tube portion 31a. As is shown in FIG. 10, the objective lens 7, image guide fiber 3 and light guide fiber 9 of the first embodiment are inserted into one of the holes (32a) in the multi-lumen tube 31.

In this case, the multi-lumen tube 31 is made of a viscoelastic material such as a synthetic resin material. The flexibility of the multi-lumen tube 31 is set to be higher than that of the image guide fiber 3. The outer diameter of the objective lens 7 is set to be greater than that of the coating portion 6 of the image guide fiber 3. For example, a forceps channel, an air-feeding/water feeding passage are formed in the other hole 32b in the multi-lumen tube 31.

In the fourth embodiment, the insertion portion 1 of the endoscope having the above structure includes the multi-lumen tube 31 of the viscoelastic material and the image guide fiber 3 of the non viscoelastic material, and the flexibility of the image guide fiber 3 is lower than that of the multi-lumen tube 31. Thus, in the fourth a embodiment, like the first embodiment, remaining bend does not easily occur in the insertion portion 1 of the endoscope. Accordingly, the possibility that bending of the insertion portion 1 bent at the time of packing and storage remains is reduced, and smoother insertion and easier operation of the insertion portion 1 of the endoscope can be achieved.

The present invention is not limited to the above embodiments, and various modifications can be made without departing the spirit of the invention.

What is claimed is:

1. An endoscope having an elastic insertion portion with an axis, comprising:
   an internal structural element extending along the axis of the insertion portion, the internal structural element being made of a non-viscoelastic material and having a flexibility; and
   a sheath element covering the internal structural element, the sheath element being made of a viscoelastic material; and
   said sheath element having a flexibility higher than the flexibility of the internal structural element, thereby preventing a remaining bend of the insertion portion.

2. The endoscope according to claim 1, wherein said internal structural element comprises an image guide fiber and a light guide fiber, and
   said sheath element is constituted by an outer tube made of a synthetic resin material.

3. The endoscope according to claim 2, wherein said image guide fiber has a concentric three-layer structure formed by:
   a picture element portion formed of a great number of optical fibers and situated at a central area of the three-layer structure,
   a jacket portion formed of a quartz glass layer in surrounding relation to the picture element portion, and
   a coating portion formed of a synthetic resin material in surrounding relation to the jacket portion.

4. The endoscope according to claim 2, wherein:
   said insertion portion includes an end portion, and an objective lens situated at a radially central area of said end portion, with an end face of the image guide fiber being fixed to the objective lens,
   said light guide fiber includes a fixed cylindrical end-fixing portion formed at an end portion of the light guide fiber, said end-fixing portion having a hollow cylindrical part, and
   said insertion portion further includes adhesive means for providing mutual fixation among the end-fixing portion of the light guide fiber, the objective lens, and the end portion of the image guide fiber such that the objective lens and the end portion of the image guide fiber are inserted in the hollow cylindrical part of the end-fixing portion.

5. The endoscope according to claim 4, wherein said image guide fiber has an outer diameter, and the objective lens has an outer diameter which is greater than the outer diameter of the image guide fiber, and an amount of filling matter contained in the outer tube in a region where the image guide fiber adjoins the light guide fiber is lower than an amount of filling matter contained in the outer tube in a region where the light guide fiber adjoins the objective lens.

6. The endoscope according to claim 2, further comprising:
   an objective lens situated at a radially central area of said end portion of the insertion portion, said objective lens being fixed to an end face of the image guide fiber; and
   a cylindrical lens frame for holding the objective lens, the cylindrical lens frame housing the objective lens and contact faces between the objective lens and the image guide fiber.

7. The endoscope according to claim 6, wherein said objective lens is constituted by a lens system having a front and a rear convex lens, said lens system being stored within the lens frame, and contact faces between the rear convex lens and the image guide fiber are contained within the lens frame.

8. The endoscope according to claim 1, wherein:
   said sheath element is constituted by a multi-lumen tube made of a synthetic resin material and having an axis and a plurality of holes extending along the axis of the multi-lumen tube, and
   said internal structural element comprises an image guide fiber and a light guide fiber inserted in one of the holes of the multi-lumen tube.

9. An endoscope having an elastic insertion portion with an axis, comprising:
   an internal structural element extending along the axis of the insertion portion, the internal structural element being made of a non-viscoelastic material and having an elasticity; and
   a sheath element covering the internal structural element, the sheath element being made of a viscoelastic material;
   said sheath element having an elasticity higher than the elasticity of the internal structural element, thereby preventing a remaining bend of the insertion portion.

10. The endoscope according to claim 9, wherein said sheath element has said elasticity and a flexibility.

* * * * *